(12) United States Patent
Petricek et al.

(10) Patent No.: US 9,447,062 B2
(45) Date of Patent: Sep. 20, 2016

(54) MANUMYCIN-TYPE METABOLITE CALLED COLABOMYCIN E WHICH INHIBITS CASPASE 1 AND CREATION OF INTERLEUKINS, STRAIN PRODUCES THE COLABOMYCIN E AND A METHOD OF A PRODUCTION OF THE COLABOMYCIN E

(71) Applicants: BIOLOGY CENTRE AS CR, v. v. i., Ceske Budejovice (CZ); INSTITUTE OF MICROBIOLOGY AS CR, v. v. i., Prague (CZ); INSTITUTE FOR CLINICAL AND EXPERIMENTAL MEDICINE, Prague (CZ)

(72) Inventors: Miroslav Petricek, Prague (CZ); Katerina Petrickova, Prague (CZ); Stanislav Pospisil, Prague (CZ); Marek Kuzma, Plzen (CZ); Alica Chronakova, Pisek (SK); Vaclav Kristufek, Ceske Budejovice (CZ); Ilja Striz, Prague (CZ)

(73) Assignees: BIOLOGY CENTRE AS CR, V.V.I., Ceske Budejovice (CZ); INSTITUTE OF MICROBIOLOGYH AS CR, V.V.I., Prague (CZ); INSTITUTE FOR CLINICAL AND EXPERIMENTAL MEDICINE, Prague (CZ)

( * ) Notice: Subject to any disclaimer, the term of this patent is extended or adjusted under 35 U.S.C. 154(b) by 0 days.

(21) Appl. No.: 14/570,862

(22) Filed: Dec. 15, 2014

(65) Prior Publication Data
US 2016/0168106 A1 Jun. 16, 2016

(51) Int. Cl.
C07D 303/00 (2006.01)
C07D 303/46 (2006.01)
C12P 13/02 (2006.01)

(52) U.S. Cl.
CPC ............. *C07D 303/46* (2013.01); *C12P 13/02* (2013.01)

(58) Field of Classification Search
CPC .... C07D 303/46; C07D 303/00; C12P 13/02
USPC ........................................................ 549/546
See application file for complete search history.

(56) References Cited

PUBLICATIONS

Petrickova et al , Biosynthesis of Colabomycin E, a New Manumycin-Family Metabolite, Involves an Unusual Chain-Length Factor, ChemBioChem, 2014, 15, p. 1334-1345.*

* cited by examiner

Primary Examiner — T. Victor Oh
(74) Attorney, Agent, or Firm — Notaro, Michalos & Zaccaria P.C.

(57) ABSTRACT

A manumycin-type metabolite called Colabomycin E which inhibits caspase 1 and creation of interleukins, strain produces the Colabomycin E and a method of a production of the Colabomycin E. Colabomycin E is a new member of the manumycin-type metabolites produced by the strain *Streptomyces aureus* SOK1/5-04 deposited in The Czech collection of microorganisms under number CCM8556. The structure of 5 is similar to that of the already known metabolite colabomycin A (3) isolated from *Streptomyces griseoflavus*. However, the upper polyene chain of 5 is two carbons longer. Therefore, it was named Colabomycin E. Biological activity assays indicated that colabomycin E significantly inhibited IL-1β release from THP-1 cells and might thus potentially act as an anti-inflammatory agent.

1 Claim, 10 Drawing Sheets

A)

R = colabomycin E (5)

R = colabomycin F (6)

R = colabomycin G (7)

R = 10

B)

R = dinorcolabomycin E (8)

R = dinorcolabomycin A (9)

Figure 1:
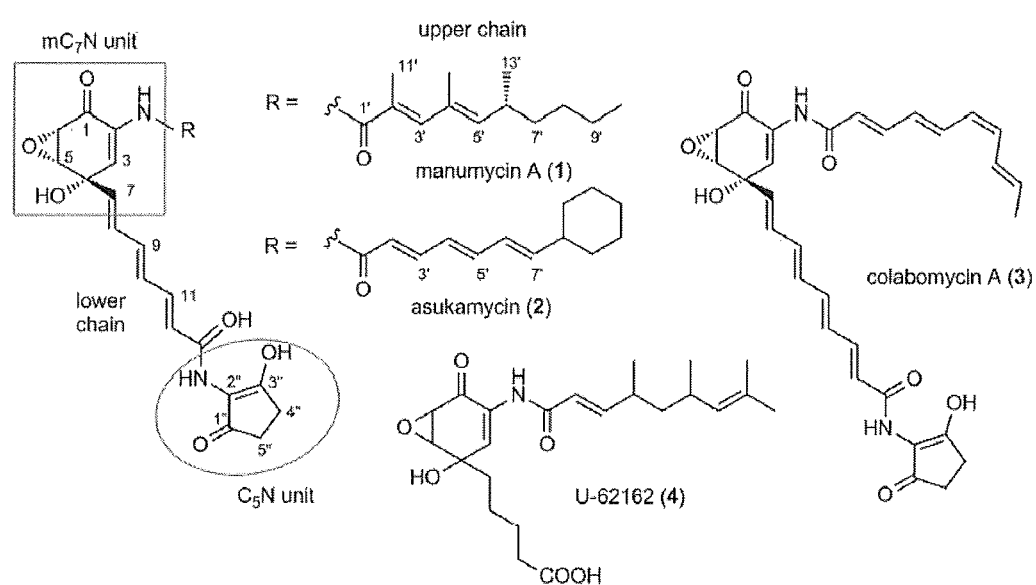

| Atom # | δ_C | m | δ_H | m | J_HH [Hz] |
|---|---|---|---|---|---|
| 1 | 190.25 | s | - | | |
| 2 | 129.17 | s | - | | |
| 3 | 129.57 | D | 7.364 | d | 2.8 |
| 4 | 71.70 | s | - | | |
| 5 | 57.78 | D | 3.785 | dd | 2.8, 4.0 |
| 6 | 53.41 | D | 3.695 | d | 4.0 |
| 7 | 138.26 | D | 6.027 | d | 14.5 |
| 8 | 131.38 | D | 6.65* | m | - |
| 9 | 136.83 | D | 6.62* | m | - |
| 10 | 134.11 | D | 6.58* | m | - |
| 11 | 141.58 | D | 6.850 | dd | 10.3, 14.8 |
| 12 | 131.70 | D | 6.57* | m | - |
| 13 | 143.48 | D | 7.371 | dd | 11.5, 14.9 |
| 14 | 122.49 | D | 6.749 | d | 14.9 |
| 15 | 167.25 | s | - | - | - |
| 1' | 165.85 | s | - | - | - |
| 2' | 124.96 | D | 6.604 | d | 14.8 |
| 3' | 141.96 | D | 7.288 | ddd | 0.4, 11.5, 14.8 |
| 4' | 131.17 | D | 6.495 | dd | 11.5, 14.8 |
| 5' | 140.98 | D | 6.820 | dd | 11.2, 14.8 |
| 6' | 133.11 | D | 6.440 | dd | 11.2, 14.6 |
| 7' | 132.91 | D | 7.077 | dd | 11.8, 14.6 |
| 8' | 127.68 | D | 6.018 | dd | 10.6, 11.8 |
| 9' | 132.71 | D | 6.111 | dd | 10.6, 11.4 |
| 10' | 128.26 | D | 6.736 | dd | 11.4, 14.9 |
| 11' | 132.96 | D | 5.862 | dq | 6.8, 14.9 |
| 12' | 18.52 | Q | 1.818 | dm | 6.8 |
| 1" | 197.08 | s | - | | |
| 2" | 115.89 | s | - | | |
| 3" | 174.74 | s | - | | |
| 4" | 32.74 | T | 2.439 | m | - |
| 5" | 25.99 | T | 2.562 | m | - |
| 4-OH | - | - | 6.351 | br s | - |
| 1'-NH | - | - | 9.186 | s | - |
| 2"-NH | - | - | 9.989 | s | - |
| 3"-OH | - | - | 14.013 | s | - |

Fig. 3

| Atom # | Colabomycin E δ_c | m | Colabomycin A δ_c | Diff. |
|---|---|---|---|---|
| 1 | 190.25 | S | 190.2 | 0.05 |
| 2 | 129.17 | S | 129.1 | 0.07 |
| 3 | 129.57 | D | 129.5 | 0.07 |
| 4 | 71.70 | S | 71.6 | 0.1 |
| 5 | 57.78 | D | 57.8 | -0.02 |
| 6 | 53.41 | D | 53.4 | 0.01 |
| 7 | 138.26 | D | 138.2 | 0.06 |
| 8 | 131.38 | D | 131.4 | -0.02 |
| 9 | 136.83 | D | 136.7 | 0.13 |
| 10 | 134.11 | D | 134.1 | 0.01 |
| 11 | 141.58 | D | 141.4 | 0.18 |
| 12 | 131.70 | D | 131.7 | 0.00 |
| 13 | 143.48 | D | 143.3 | 0.18 |
| 14 | 122.49 | D | 122.5 | -0.01 |
| 15 | 167.25 |  | 167.1 | 0.15 |
| 1' | 165.85 | S | 165.8 | 0.05 |
| 2' | 124.96 | D | 125.0 | -0.04 |
| 3' | 141.96 | D | 142.1 | -0.14 |
| 4' | 131.17 | D | 131.1 | 0.07 |
| 5' | 140.98 | D | 136.1 | 4.88 |
| 6' | 133.11 | D | 127.1 | 6.01 |
| 7' | 132.91 | D | 134.1 | -1.19 |
| 8' | 127.68 | D | 128.2 | -0.52 |
| 9' | 132.71 | D | 133.6 | -0.89 |
| 10' | 128.26 | D |  |  |
| 11' | 132.96 | D |  |  |
| 12' | 18.52 | Q | 18.5 | 0.02 |
| 1'' | 197.08 | S | n.d. |  |
| 2'' | 115.89 | S | 115.7 | 0.19 |
| 3'' | 174.74 | S | n.d. |  |
| 4'' | 32.74 | T | n.d. |  |
| 5'' | 25.99 | T | n.d. |  |

Fig. 4

| Bacterial strain | | Amount of colabomycin E per disc | | | Strain features |
|---|---|---|---|---|---|
| | | 3 µg | 12 µg | 30 µg | |
| Gram⁻ | *E.coli* ATCC® 25922 (CNCTC 5276) | 6 | 6 | 6 | |
| | *Pseudomonas aeruginosa* ATCC® 27853 (CNCTC 5482) | 6 | 6 | 6 | |
| Gram⁺ | *Staphylococcus aureus* ATCC® 25923 (CNCTC 5481) | 7 | 8 | 9 | |
| | *Staphylococcus aureus* ATCC® 29213 (CNCTC 5480) | 6 | 7 | 8 | |
| | *Staphylococcus aureus* ATCC® 43300 (CNCTC 6271) | 6 | 7 | 8 | methicillin$^R$, oxacillin$^R$ |
| | *Staphylococcus epidermidis* ATCC® 14990 (CNCTC 5671$^T$) | 6 | 7 | 8 | |
| | *Staphylococcus haemolyticus* ATCC® 29970 (CNCTC5674$^T$) | 6 | 6 | 7 | |
| | *Enterococcus faecalis* ATCC® 29212 (CNCTC 5483) | 6 | 6 | 6 | |
| | *Enterococcus faecalis* ATCC® 51299 (CNCTC 5530) | 6 | 6 | 6 | VanB, low-level vancomycin$^R$ |
| | *Enterococcus faecium* CNCTC 5773 | 6 | 6 | 7 | |
| | *Streptococcus pneumoniae* ATCC® 49619 (CNCTC 5043) | 10 | 10 | 11 | |
| | *Streptococcus pneumoniae* CNCTC 5635 | 9 | 10 | 10 | |
| | *Streptococcus pneumoniae* CNCTC 5636 | 8 | 9 | 10 | |
| | *Streptococcus pyogenes* ATCC® 12344 (CNCTC 7155$^T$) | 8 | 9 | 10 | |
| | *Streptococcus agalactiae* ATCC® 12378 (CNCTC 6588$^T$) | 7 | 8 | 9 | |

Fig. 10

US 9,447,062 B2

MANUMYCIN-TYPE METABOLITE CALLED COLABOMYCIN E WHICH INHIBITS CASPASE 1 AND CREATION OF INTERLEUKINS, STRAIN PRODUCES THE COLABOMYCIN E AND A METHOD OF A PRODUCTION OF THE COLABOMYCIN E

FIELD OF THE ART

Manumycin-type metabolites with significant inhibiting effect of caspase 1 and creation of interleukins.

STATE OF THE ART

The group of manumycin-type antibiotics is represented by slightly more than 30 metabolites produced by the genus *Streptomyces*. The structures of these compounds are typified by the presence of two carbon chains ("upper" and "lower") connected in meta fashion to an unusual central epoxyquinone moiety. This core structure consisting of a 2-amino-5,6-epoxy-4-hydroxycyclohex-2-en-1-one (mC7N unit) is particularly characteristic for the group. In some cases, however, its oxirane ring is replaced by a hydroxyethylene unit at C5/C6, and these compounds are designated as type II manumycins. The third most distinguishing structural feature after the core unit and carbon chains is the so-called C5N unit represented by the 2-amino-3-hydroxycyclopent-2-en-1-one moiety, which in most cases terminates the lower carbon chain. [1] In addition to its chromophoric features, the structure likely acts as a pharmacophore. [2] The most prominent structural variations of manumycins are found in the upper side chain and involve the pattern of methyl branches, the number and positions of the double bonds, and the chain length. The lower chain extending from the mC7N is usually represented by an all-trans triene. However, examples with altered lower chain shape, involving trans tetraene or saturated five-carbon chains, can also be found. Most members of the manumycin-group metabolites have been discovered by biological screening for antibiotic, antifungal, [1] insecticidal, and cytotoxic [3] activities and inhibition of enzymes, including inhibition of RAS farnesyltransferase, [4] caspase (ICE), [5] IκB kinase, [6] neutral sphingomyelinase, [7] and acetylcholinesterase. [8] They are thus drug candidates to treat cancer, atherosclerosis, inflammation, and Alzheimer's disease. Because individual members of the manumycin family show different activities in particular inhibitory assays, the structural variations in the upper chain are likely the major factor affecting the specificities of those compounds. Apart from that, the epoxyquinol moiety is crucial for antibacterial activity [3].

Studies on the manumycin family antibiotics have focused mainly on manumycin A and asukamycin. [9-14] The biosynthetic gene cluster of asukamycin from *Streptomyces nodosus* ssp. *asukaensis* has been identified and characterized, [15] and details of the enzymatic mechanism of formation of the epoxyquinone moiety mC7N have most recently been described. [16] Inspection of the asukamycin biosynthetic gene cluster revealed the presence only of type II iterative polyketide synthase genes that were involved in the biosynthesis of both carbon chains. [15] This was in contrast with some previous assumptions that assumed participation of modular PKSs instead. [12, 17] The details of the C5N ring formation were also clarified in the above and other recent works. [2, 15, 18] The unusual enzyme 5-aminolevulinate synthase (ALAS) of *S. nodosus* ssp. *Asukaensis* is engaged not only in ALA formation but also in cyclization of ALA-CoA to form the C5N unit. The occurrence of the ALAS genes (homologues of *S. nodosus* ssp. *asukaensis* asuD2) in *Streptomyces* can be used as a very simple indicator of the C5N biosynthetic route [18] and hence might serve as a screening tool for identification of new manumycin-type antibiotic producers.

Screening the environment for putatively new bioactive natural compounds is of great interest, because it possesses huge uncovered microbial diversity (http://www.terragenome.org). [19, 20] Moreover, human-disturbed environments have not yet been satisfactorily exploited. Streptomycetes serve as a very good target for genetic screening based on cultivation because they offer tremendous biochemical diversity [21] and they can be isolated from the environment with very high recovery. Cultivation-based techniques accompanied by focused and specific genetic screening are thus still a successful strategy in searching for new valuable bioactive compounds.

In general, manumycins do not show significant antibacterial effects. However, as has been already documented, particularly in the case of manumycin A, they exhibit strong enzyme-inhibitory features and specifically affect a number of crucial mammalian enzymes. The particular structure of the polyketide chains seems to affect the individual inhibitory activities and modulates the overall effect of the compound on the cell. While the strong pro-apoptotic character of the most studied manumycin A led to its widespread evaluation in the field of anticancer research.

DESCRIPTION OF THE INVENTION

Colabomycin E is a new member of the manumycin-type metabolites produced by the strain *Streptomyces aureus* SOK1/5-04 deposited in The Czech collection of microorganisms under number CCM8556 and identified by genetic screening from a library of streptomycete strains.

Colabomycin E belongs to the pharmaceutically attractive manumycin compound family. The structures of colabomycin E and accompanying congeners were resolved. The entire biosynthetic gene cluster was cloned and expressed in *Streptomyces lividans*. Bioinformatic analysis and mutagenic studies identified components of the biosynthetic pathway that are involved in the formation of both polyketide chains. Recombinant polyketide synthases (PKSs) assembled from the components of Colabomycin E and asukamycin biosynthetic routes catalyzing the biosynthesis of "lower" carbon chains were constructed and expressed in *S. aureus* SOK1/5-04 ΔcolC11-14 deletion mutant. Analysis of the metabolites produced by recombinant strains provided evidence that in both biosynthetic pathways the length of the lower carbon chain is controlled by an unusual chain-length factor supporting biosynthesis either of a triketide in asukamycin or of a tetraketide in Colabomycin E. Biological activity assays indicated that colabomycin E significantly inhibited IL-1β release from THP-1 cells and might thus potentially act as an anti-inflammatory agent.

Here we report the isolation of the streptomycete strain producing a new manumycin-type metabolite designated Colabomycin E. A new variant of the short-chain chain-length factor (CLF) is involved in the control of its lower polyketide chain biosynthesis. Overall characteristics of the colabomycin E antibacterial, anti-inflammatory, and proapoptotic activities were assessed.

Bacterial strain *Streptomyces aureus* SOK1/5-04 was isolated from colliery spoil heaps (North West Bohemia, Sokolov Coal Basin) on McBeth Scale agar. The strain was collected from the top layer (0-5 cm) of a one-year-old heap consisting of excavated tertiary lacustrine sediments (pH 8.39).

Fermentations of the wild-type strain yielded several compounds putatively falling into the manumycin family were determined The structures of 5 and 7 were determined by a combination of $^1$H NMR, 1 $^{13}$C NMR, gCOSY, J-resolved, gHSQC, gHMBC, gHSQC-NOESY, and 1D TOCSY techniques, as well as by HRMS.

The structure of 5 is similar to that of the already known metabolite colabomycin A (3) isolated from *Streptomyces griseoflavus*. However, the upper polyene chain of 5 is two carbons longer. Therefore, it was named Colabomycin E.

In contrast to manumycin A, the less pro-apoptotic colabomycin E may have particular application as an anti-inflammatory agent. Similarly, quite recently, macrolides of a clarithromycin type, routinely used as antibiotics, were "rediscovered" as potent inhibitors of inflammation

FIGURES

FIG. 1: Structures of manumycin-type antibiotics

Figure 2:
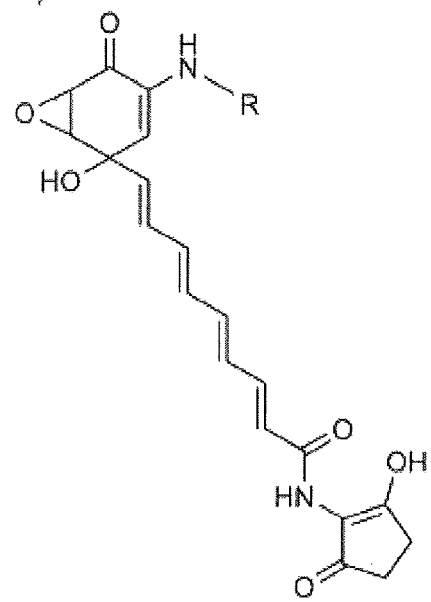
Figure 2:
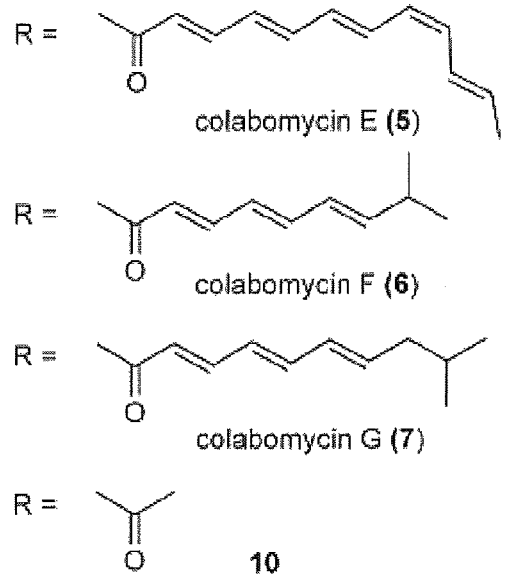
Figure 2:
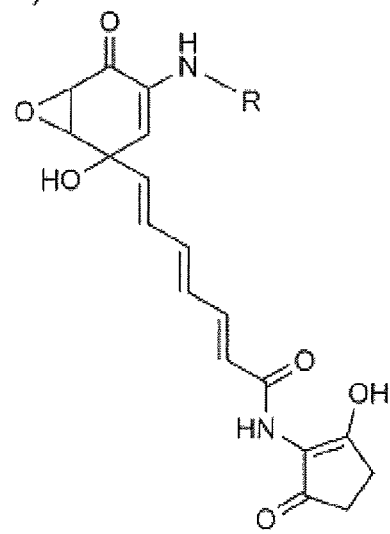
Figure 2:
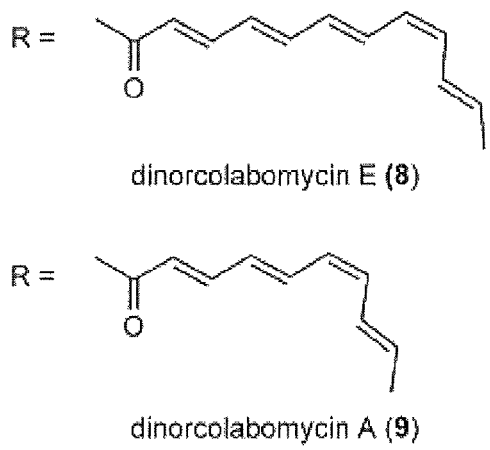

FIG. 2: Structures of novel manumycin-type metabolites. Compounds were isolated (A) from the wild-type *S. aureus* SOK1/5-04 strain and from colC3C4C5 mutant (10), and (B) from recombinant strains expressing heterologous PKS involved in the lower chain assembly.

FIG. 3: $^1$H and $^{13}$C NMR data of colabomycin E 5 (600.23 MHz for $^1$H, 150.94 MHz for $^{13}$C, DMF-d$_7$, 30° C.)

Figure 5A:
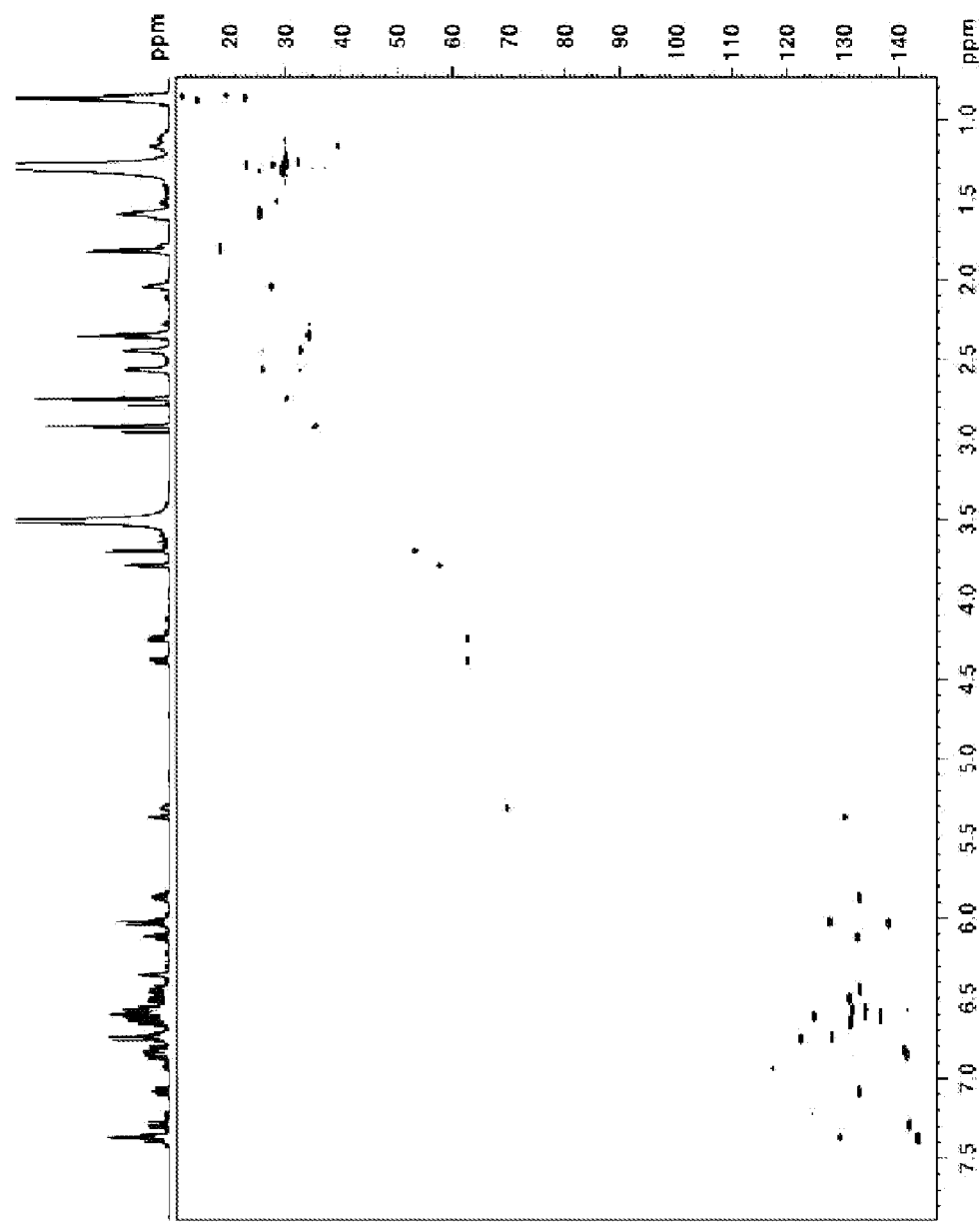
Figure 5B:
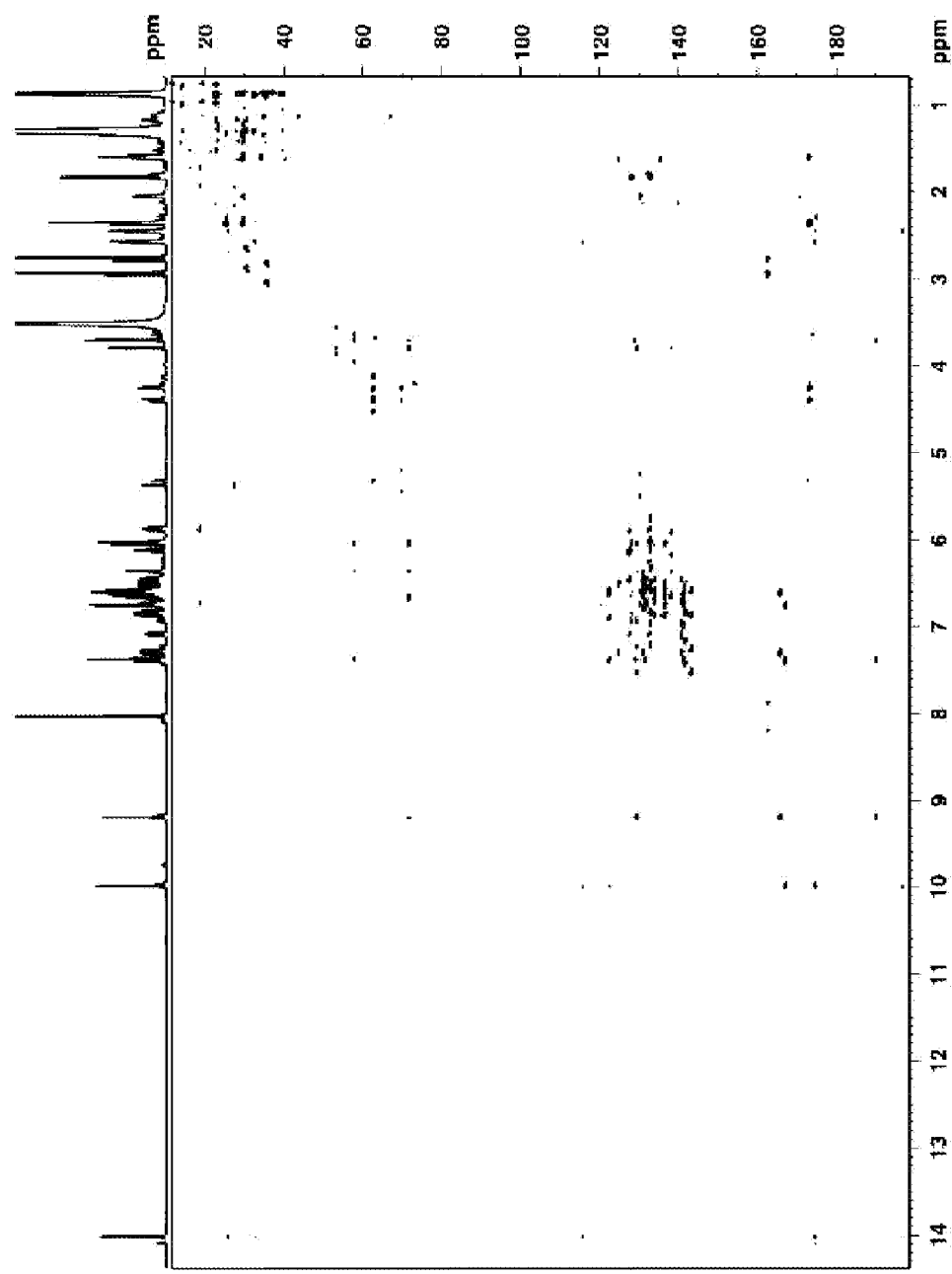
Figure 5C:
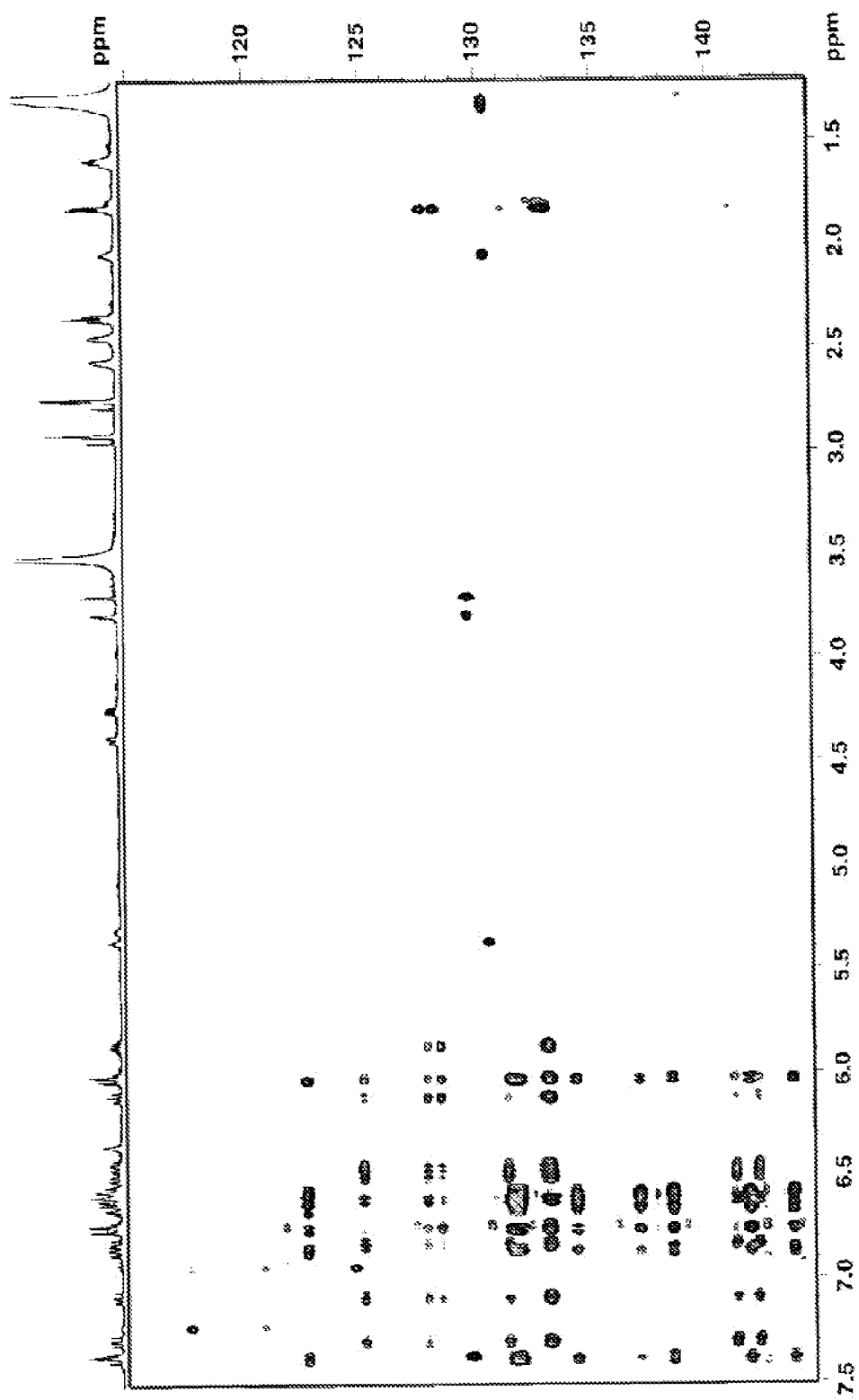

FIG. 4: Comparison of $^{13}$C NMR signals of colabomycin E and colabomycin A. Data for Colabomycin A FIGS. 5A, 5B, 5C: $^1$H-$^{13}$C HSQC spectrum, B) $^1$H-$^{13}$C HMBC spectrum and C) $^1$H-$^{13}$C HSQC-TOCSY of colabomycin E 5 (600.23 MHz for $^1$H, 150.94 MHz for $^{13}$C, DMF-d$_7$, 30° C.)

Figure 6:
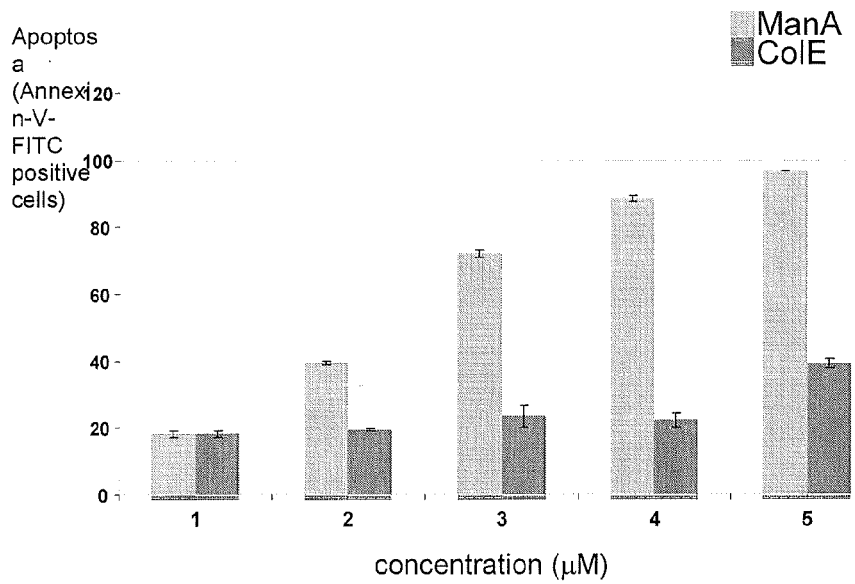

FIG. 6: Pro-apoptotic effect of manumycins to leukemic cells Jurkat (after 4 hours); ManA: manumycin A, ColE: colabomycin E FIG. 7: Proapoptotic and anti-inflammatory features of colabomycin E relative to manumycin A Inhibition of IL-1b processing in human THP-1 macrophages stimulated by TNFa [50 ng mL$^{-1}$]. The amounts of released active form of IL-1b are plotted against rising concentrations of colabomycin E (&) and manumycin A (*). The THP-1 cell viability began to decrease with concentrations of 2 mm or higher, and under these circumstances activation of caspase-1 might lead to a potentiation of IL-1b release. The amounts of released active form of IL-1b are plotted against rising concentrations of colabomycin E and manumycin A. The THP-1 cell viability began to decrease with concentrations of 2 mm or higher, and under these circumstances activation of caspase-1 might lead to a potentiation of IL-1b release.

Figure 8:
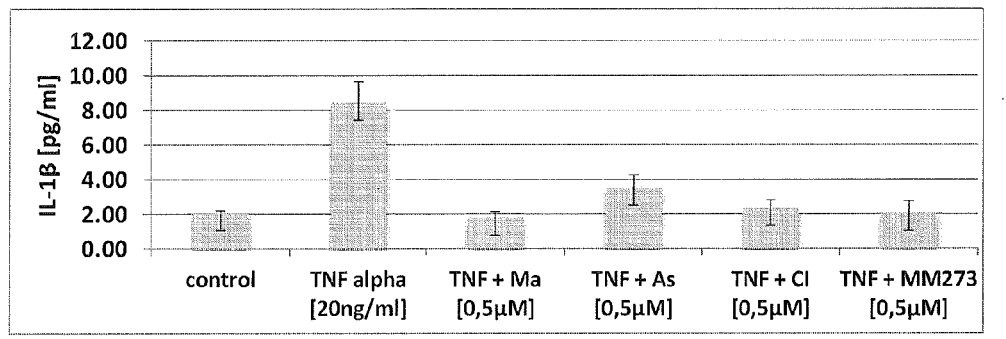
Figure 9:
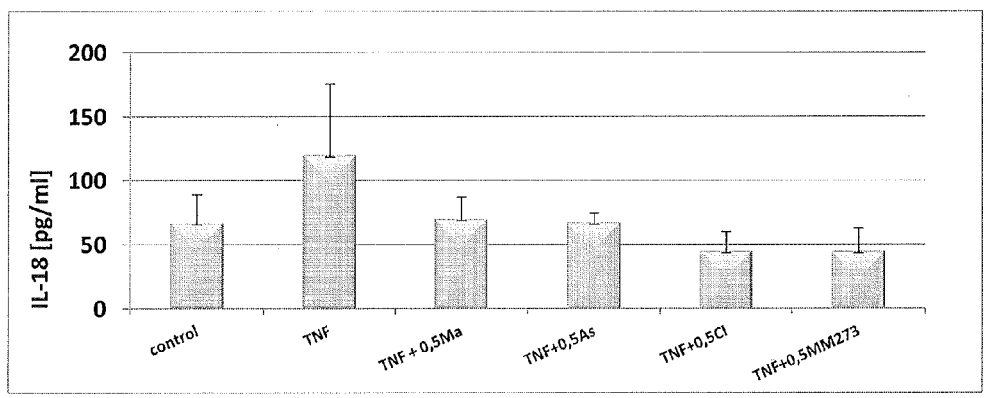

FIG. 8: Influence of manumycins (0.5 µM) to production of IL-1β; Ma—manumycin A, As—asukamycin, MM273—colabomycin E, CI—caspase synthetic inhibitor (Ac-YVAD-CHO)Fi FIG. 9: Influence of manumycins (0.5 µM) to production of IL-18; Ma—manumycin A, As—asukamycin, MM273—colabomycin E, CI—caspase synthetic inhibitor (Ac-YVAD-CHO).

FIG. 10: Antibacterial features of colabomycin E—disc diffusion method. Colabomycin E samples were applied to standard 6 mm discs; therefore the zone diameters bellow 7 mm mean no growth inhibition. The strains kindly provided by the Czech National Collection of Type Cultures.

EXAMPLES OF THE INVENTION

Example 1

Streptomycete bacterial strains were isolated from environmental samples, including agricultural soil, colliery spoil heaps under different succession development, cave sediments and Tertiary lacustrine clay sediments excavated from underground. Screening was made with the help of genetic marker—ALAS-encoding gene (asuD2 homologue), which indicates the putative presence of the biosynthetic pathway for the C5N unit present in most of the manumycin-type antibiotic. Southern blot hybridization with Dig-labeled DNA probe was used for this purpose.

The DNA probe (prepared from the cloned fragment of *S. nodosus* subsp. *asukaensis* genomic DNA) was excised from pMPH25 as a 0.3-kb SacII fragment (hemA-asuA probe) and labeled by random primed non-radioactive (Dig-) labeling method. 1 µg of DNA fragment was denaturated by 10 min heating at 95° C. and by quick chilling in ice. The reaction proceeded at 37° C. overnight and the mixture (20 µl) consisted of the DNA fragment, random hexanucleotides, reaction buffer, and 2 U of Klenow fragment. The reaction was stopped by adding 2 µl 0.5 M EDTA pH8, and the labeled DNA was precipitated with 2 µl 4 M LiCl and 60 µl EtOH for two hours at −70° C. Hybridizations were performed at 68° C. overnight. All posthybridization washings were carried out with 2×SSC (1×SSC is 0.15 M NaCl plus 0.015 M sodium citrate), 0.1% sodium dodecyl sulfate (SDS). The first two washings proceeded at room temperature for 2×5 min, the second two washings were at 45° C. for 2×15 min.

Positive strain SOK1/5-04 was submitted into the Culture Collection of Soil Actinomycetes České Budějovice (CCACB) under CCSACB No. 5 as well as other strains. Bacterial cultures are long-term maintained as spore suspensions in glycerol (15% v/v) at −80° C. and freeze-dried.

Isolation and characterization of metabolites produced by *S. aureus* SOK1/5-04

Fermentations of the wild-type strain yielded several compounds putatively falling into the manumycin family as determined by indicative TLC and LC-MS. Chromatograms detected one major and three accompanying minor compounds, providing molecular ions of 555.2, 529.2, 531.2, and 545.2 in their negative ion mass spectra (FIG. 2). The structures of 5 and 7 were determined by a combination of $^1$H NMR, $^{13}$C NMR, gCOSY, J-resolved, gHSQC, gHMBC, gHSQC-NOESY, and 1D TOCSY techniques, as well as by HRMS. The conjugated polyenoic acid structure of 5 is consistent with the distinct absorbance spectrum of this compound (lmax=200, 262, 362 nm). NMR spectral data are summarized in FIGS. 3 and 4

The 3JH,H coupling constants observed for the upper polyene chain show E stereochemistry at all double bonds with one exception: namely the double bond between C-8' and C-9', which has the quite infrequent (in polyketides) Z configuration. This was also confirmed by a NOE contact between H-8' and H-9' detected in the HSQC-NOESY spectrum. The structure of 5 is similar to that of the already known metabolite colabomycin A (3) isolated from *Streptomyces griseoflavus*. However, the upper polyene chain of 5 is two carbons longer. Therefore, it was named Colabomycin E.

Apart from that of colabomycin E ($C_{32}H_{32}N_2O_7$, d=−0.2 ppm, m/z found: 555.2131 [M-H]$^-$), molecular ions of the next three compounds observed by HRMS were consisted with the molecular formulas of colabomycin A (3;

$C_{30}H_{30}N_2O_7$, m/z 529.1974 [M-H]⁻, d=−0.2 ppm) and two other branched congeners, designated as colabomycin F (6; $C_{30}H_{32}N_2O_7$, m/z 531.2130 [M-H]⁻, d=−0.2 ppm) and G (7; $C_{31}H_{34}N_2O_7$, m/z 545.2292 [M-H]⁻, d=0.7 ppm).

Feeding the culture of *S. aureus* SOK1/5-04 Δcol16 mutant with leucine resulted in a 2.5-fold increase in colabomycin G (7) production relative to colabomycin A. NMR analysis of the compound revealed two isolated unsaturated polyene chains with strongly overlapped signals in the ¹H NMR spectrum. The upper chain of the molecule exhibited a well-resolved spin system of three double bonds with a —CH₂CH(CH₃)₂ moiety at the end. This observation was similar to that made in asukamycin producer feeding experiments and indicated that 3-methylbutyryl-CoA presumably served as a starter unit in the upper polyketide chain biosynthesis of 7.

Example 2

Fermentation, Extraction and Isolation of Manumycint-Type Metabolites

*S. aureus* SOK1/5-04 production culture was grown in 60 ml of medium in a 500 ml baffled Erlenmeyer flask on a rotary shaker (160 rpm, 28° C., 84 h). Each flask was inoculated by 6 ml of 48 h old seed culture. The used culture medium: Glycerol, 3 g; Yeast extract, 4 g; Malt extract, 10 g; NZ Amine A, 1 g; NaCl, 2 g; OB Salts, 3 ml; pH 7.3, in 1000 ml H2O. OB Salts: CuSO4.5H2O, 0166 g; FeSO4.7H2O, 0.25 g; MnSO4.5H2O, 0.12 g; CaCl2.2H2O, 0.5 g; ZnSO4.7H2O, 0.3 g, in 100 ml H2O The recombinant cultures of *S. coelicolor* M512 and *S. lividans* K4-114 used for heterologous expression of col cluster were fermented in the same medium under identical cultivation conditions. In feeding experiment, amino acid L-leucine was added to production medium (3.5 g/l) before sterilization. At the end of fermentation, the mycelium was collected by centrifugation and extracted with methanol. After evaporation under reduced pressure, the crude extract was re-extracted with chloroform and crystallized. In the typical experiment, mycelium obtained from 28 flasks (1.7 l) afforded about 55 mg of crystalline colabomycin E. Colabomycin G was isolated after cultivation of *S. aureus* SOK1/5-04 ΔcolC16 mutant in production medium enriched with L-leucine. Antibiotics from the crude methanol extract of mycelium were re-extracted into chloroform. This extract was first purified by column chromatography (silica gel 60) with the mobile phase consisting of heptane-ethyl acetate-methanol (5:4:1). The products were further repeatedly purified using a Sephadex LH-20 or Toyopearl HW-40 F columns and eluted with methanol. Fractions were evaluated by TLC (silica gel 60 F254; Merck) developed with heptane-ethyl acetate-methanol (5:4:1). The compound was detected as single spots by UV absorption at 254 and 360 nm.

Example 3

Analysis of Colabomycin Metabolites

UHPLC-DAD-ToFMS analyses were carried out on UPLC System. The LCT orthogonal accelerated time of flight mass spectrometer with an electrospray interface was operating in both positive and negative ion mode. Full scan spectra from m/z 100 to 1200 were acquired with a scan time of 0.1 s and 0.01 s interscan delay. The fragmentation using in-source collision induced dissociation (CID) was achieved by the Aperture I value set to 50, 75, and 100 V. Mass Lynx V4.1 software was used for data processing. Analyses were performed on Acquity UPLC BEH C18 column (50×2.1 mm i. d; 1.7 μm) with the mobile phase flow rate of 0.4 mL min⁻¹, column temperature of 25° C., and injection volume of 1 μL. The mobile phase consisted of (A) formic acid-water (0.1:99.9, v/v), and (B) ACN using gradient elution program (min/% A): 0.0/90.0, 12.0/40.0, 15.0/20.0, 16.0/20, followed by 2.0 min wash step with 100% B. After acquisition, the specific [M-H]⁻ ions were extracted with 0.02 Da extraction mass window. For compounds' identity verification, the parameters set for Elemental Composition editor were: CHNO algorithm; mass measurement error tolerance, 5 mDa; i-FIT (norm) error, 5. Fragmentation using CID was employed for verification of generated fragment ions with a mass measurement error tolerance of 10 mDa set in Mass Fragment software.

NMR spectra were recorded on a Bruker Avance III 600 (600.23 MHz for ¹H, 150.94 MHz for ¹³C) DMF-d₇ at 30° C. Residual signals of solvent were used as an internal standard ($\delta_H$ 2.743 ppm, $\delta_C$ 30.11). NMR experiments: ¹H NMR, ¹³C NMR, gCOSY, J-resolved, gHSQC, gHMBC, and 1D TOCSY were performed using the manufacturer's software. ¹H NMR and ¹³C NMR spectra were zero filled to fourfold data points and multiplied by window function before Fourier transformation. Two-parameter double-exponential Lorentz-Gauss function was applied for ¹H to improve resolution and line broadening (1 Hz) was applied to get better ¹³C signal-to-noise ratio. Chemical shifts are given in δ-scale with digital resolution justifying the reported values to three ($\delta_H$) or two ($\delta_C$) decimal places.

Example 4

Biological Activities of Colabomycin E

Figure 7:
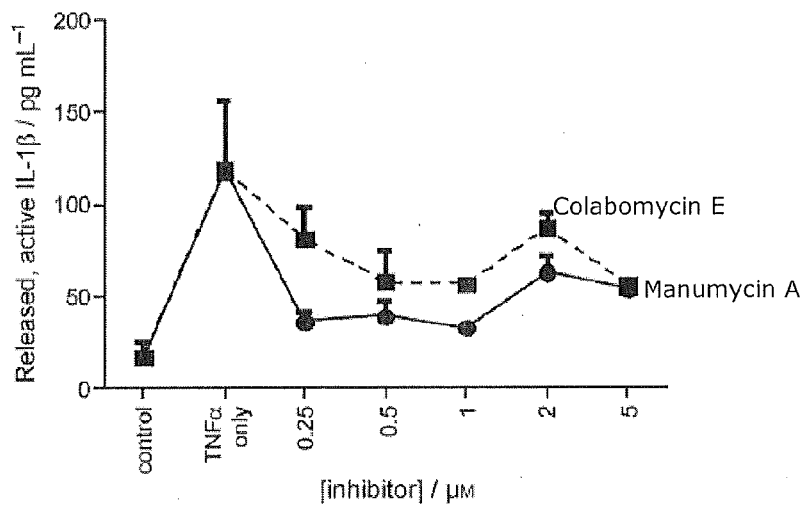

Colabomycin E exhibits similar activities as other members of the manumycin family. Similarly to manumycin A and others, the anti-bacterial effects are quite mild, the compound in higher concentrations suppresses growth of Gram⁺ bacteria, mainly staphylococci and streptococci, and has no effect on Gram⁻ (FIG. 9. Colabomycin E at 5 μM concentration also possesses weak pro-apoptotic features when assayed on human leukemic Jurkat cells. However, the pro-apoptotic effect is substantially weaker than that of the potent anticancer compound manumycin A (FIG. 6). The most prominent anti-inflammatory effect, caused by the inhibition of caspase 1, was assayed using human THP-1 macrophage cells. Caspase 1 is a crucial enzyme in the processing of active forms of several important pro-inflammatory cytokines. Both colabomycin and manumycin A significantly inhibited IL-1β beta release from THP-1 cells starting from a concentration of 0.25 μM and the dose curve reached an inhibitory plateau at 0.5 μM concentration for both substances (FIG. 7). Furthermore, in other experiments, colabomycin E (at 0.5 μM concentration) was found to inhibit also IL-6, IL-8, and IL-18 production in THP-1 cells stimulated with TNFα

Bioactivity Analysis

Antibacterial activity of colabomycin E was tested by disc diffusion method. The strains were cultivated on MH agar plates at 36° C., aerobically for 18 hrs. For streptococci the media was supplemented with 5% sheep blood and the bacteria were cultivated aerobically for 20 hrs in 5% CO₂. Colabomycin E samples dissolved in dioxane were applied to standard 6 mm discs; therefore zone diameters below 7 mm indicate no growth inhibition. The anti-inflammatory effect of colabomycin E was assayed on the TNFα-stimulated human monocyte/macrophage cell line THP-1. The cells were cultured in RPMI-1640 medium, supplemented with 10% heat inactivated fetal calf serum (FCS), L-glutamine, penicillin and streptomycin. Cells were seeded into 6-well tissue culture plates at a density of $2\times10^6$ cells per 2 ml per well and cultured under a 5% $CO_2$ atmosphere at 37° C. THP-1 cells were stimulated with TNFα (50 ng/ml) under serum free conditions in the presence of colabomycin or manumycin A.

Unstimulated cells were used as controls. IL-1β release was measured through flow cytometry in culture supernatants by Fluorokine MAP human base kit A using the Luminex[100] System. In the first step, 50 µl of the samples/standards were incubated with 50 µl of microparticles for 3 hours at RT on a horizontal orbital microplate shaker. After washing the unbound substances, 50 µl of the secondary antibodies conjugated with biotin was added to each well and incubated the samples/standards for another 1 hour. After the incubation, the unbound secondary antibodies were washed and 50 µl of the Streptavidin-PE was added. After the 30 minutes of incubation, the samples/standards were washed and resuspended the microparticles in 100 µl of wash buffer. Samples/standards were read using a Luminex analyzer.

Proapoptotic features were assayed using human Jurkat cells. The cells were cultivated in RPMI medium supplemented with 10% FBS and antibiotics. Just before experiments cells were plated into the fresh medium at $4\times10^5$ cells/ml in 24-well cultivation plates. They were treated with increasing concentrations of manumycin A (positive control) and colabomycin E for 4 hours. Cells were then harvested by centrifugation and apoptotic cells were labeled by Annexin V-FITC. The stained cells were subsequently analyzed by flow cytometry analysis in a Guava EasyCyte flow cytometer and the obtained data were evaluated using FlowJo software.)

INDUSTRIAL APPLICABILITY

Production of new types of antibiotics. Anti-inflammatory treatment, design of new therapeutic agent with anti-inflammatory effect.

The invention claimed is:
1. A manumycin-type metabolite called Colabomycin E which inhibits caspase 1 and creation of interleukins IL-1, IL-1β, IL-6, IL-8 having a structure:

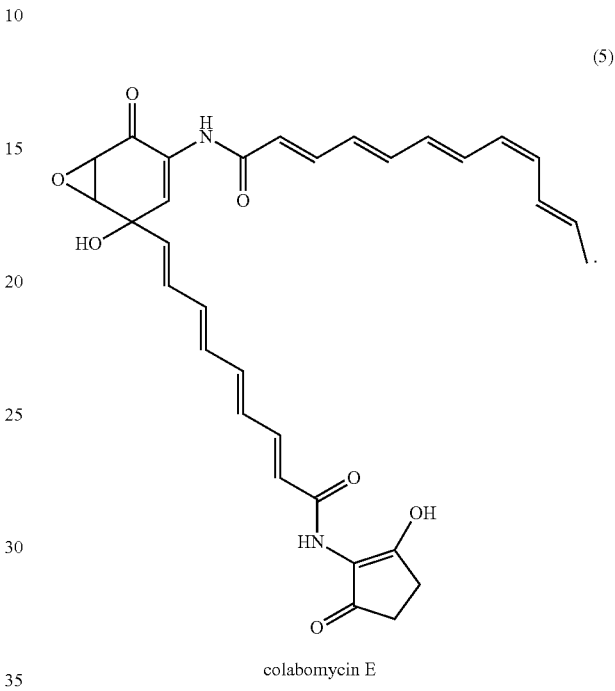

colabomycin E (5)

* * * * *